United States Patent [19]

Goble et al.

[11] Patent Number: 5,284,142
[45] Date of Patent: Feb. 8, 1994

[54] THREE-DIMENSIONAL IMPEDANCE IMAGING PROCESSES

[75] Inventors: John C. Goble; David Isaacson, both of Latham; Margaret Cheney, Troy, all of N.Y.

[73] Assignee: Rensselaer Polytechnic Institute, Troy, N.Y.

[21] Appl. No.: 808,795

[22] Filed: Dec. 16, 1991

[51] Int. Cl.$^5$ .............................................. A61B 5/05
[52] U.S. Cl. ............................. 128/653.1; 364/413.13
[58] Field of Search ...................... 128/734; 364/413.13

[56] References Cited

U.S. PATENT DOCUMENTS

| | | | |
|---|---|---|---|
| 4,486,835 | 12/1984 | Bai et al. | 128/734 |
| 4,539,640 | 9/1985 | Fry et al. | 128/734 |
| 4,617,939 | 10/1986 | Brown et al. | 128/734 |
| 4,920,490 | 4/1990 | Isaacson | 128/734 |
| 5,184,624 | 2/1993 | Brown et al. | 128/734 |

Primary Examiner—Ruth S. Smith
Attorney, Agent, or Firm—Notaro & Michalos

[57] ABSTRACT

A method of practicing electrical impedance tomography produces three-dimensional images of a body. First, one applies certain special current patterns to the body through an array of electrodes attached to the surface. For each current pattern, one measures the voltage at each electrode, thus obtaining a corresponding pattern of voltages. These data are then used in a certain special reconstruction process, which enables a full three-dimensional reconstruction to be done in a short time. The result is a display of an approximation to the electric conductivity and/or electric permittivity in the interior of the body.

8 Claims, 1 Drawing Sheet

THREE-DIMENSIONAL IMPEDANCE IMAGING PROCESSES

FIELD AND BACKGROUND OF THE INVENTION

The present invention relates in general to electrical impedance tomography and in particular, to a new and useful method and apparatus for producing a three-dimensional impedance image of the interior of a body, despite the tremendous number of computations which were hitherto thought essential in creating such an image.

The present invention has applications in medical imaging, clinical monitoring, non-destructive evaluation, process control and the imaging of multiphase fluid flow.

Although superficially similar to X-ray computed tomography or positron emission tomography, electrical impedance tomography (EIT) encounters fundamentally different problems when attempting to create an image. In X-ray computer tomography, for example, the paths of photons through the body are essentially straight lines. In contrast, current paths in EIT are functions of an unknown resistivity distribution. This gives rise to a non-linear reconstruction problem.

The physiological basis for EIT, relies on the fact that biological tissues contain free charge carrier that permit them to act as relatively poor electrical conductors. This ability to conduct electricity varies substantially among the various body tissues. Some typical values for resistivity of biological tissues are disclosed in Table 1. The goal of EIT is to compute and display the spatial distribution of resistivity inside the body.

TABLE 1

| Material | Resistivity ($\rho$) ohm-cm |
|---|---|
| Blood | 150 |
| Plasma | 63 |
| Cerebrospinal Fluid | 65 |
| Urine | 30 |
| Skeletal muscle | 300 |
| Cardiac muscle | 750 |
| Lung | 1275 |
| Fat | 2500 |
| Copper | $1.724 \times 10^{-6}$ |

The present invention is related to the subject matter of U.S. Pat. No. 4,920,490 issued to one of the co-inventors of the present application and incorporated here by reference.

This invention is also related to U.S. patent application Ser. No. 07/727,075 entitled A LAYER STRIPPING PROCESS FOR IMPEDANCE IMAGING, which is also incorporated here by reference and which discloses mathematical theories and manipulations which are useful in understanding the present invention. For additional disclosure concerning hardware useful in practicing the present invention, see U.S. patent application Ser. No. 07/734,591 entitled CURRENT PATTERNS FOR ELECTRICAL IMPEDANCE TOMOGRAPHY which is also incorporated here by reference.

SUMMARY OF THE INVENTION

The present invention is drawn to a further process for EIT which is particularly useful in producing three-dimensional images.

An object of the present invention is to provide a method of three-dimensionally imaging the interior of a body using electrical impedance tomography, comprising: applying an electrode array having a first selected number of electrodes (L) to the surface of the body; applying a second selected number of special current patterns to the electrode array, these current patterns being either a) tensor products of discrete trigonometric functions, or b) the best patterns with which to represent the boundary map R, or c) the best patterns with which to distinguish the internal resistivity from some guess for the internal resistivity; measuring a number of voltage patterns, which is equal to the second selected number, resulting from application of the current patterns, using a fast process for reconstructing an approximation to the internal resistivity, in which the resistivity $\rho^1$ is expressed in terms of a finite-dimensional basis, and its coefficients in this basis are given by equation (10) which is in the following, where $\rho^0$ is defined by equation (17) in the following, $F(\rho^0)$ is defined by equation (9), and the matrix F' is defined by equation (12) or by the approximation of equation (16); using a method for inverting the matrix defined by (12) or (16), wherein the eigenvectors and eigenvalues of the appropriate matrix are found and stored, and the matrix inverse computed according to the spectral theorem, so that the matrix inversion is reduced to the computation of a plurality of inner products.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

In EIT, one applies small alternating currents through electrodes attached to the skin, and measures the resulting voltages. From Maxwell's equations, we can obtain the governing equation, $$\nabla \cdot (\sigma + i\omega\epsilon) \nabla u = 0 \qquad (1)$$

inside the body $\Omega$, where u is the electric potential, $\epsilon$ is the electric permittivity, $\sigma$ is the conductivity, and $\omega$ is the frequency of the applied current. For simplicity, we will consider the case $\omega = 0$, but the invention applies equally well to the case when $\omega \neq 0$. Since currents are applied through electrodes on the skin, a current density is established whose inward pointing normal j is $$\sigma \frac{\partial u}{\partial \nu} = j \text{ on } \partial\Omega. \qquad (2)$$

We now introduce a notation for the three dimensional EIT problem.

Figure 1:
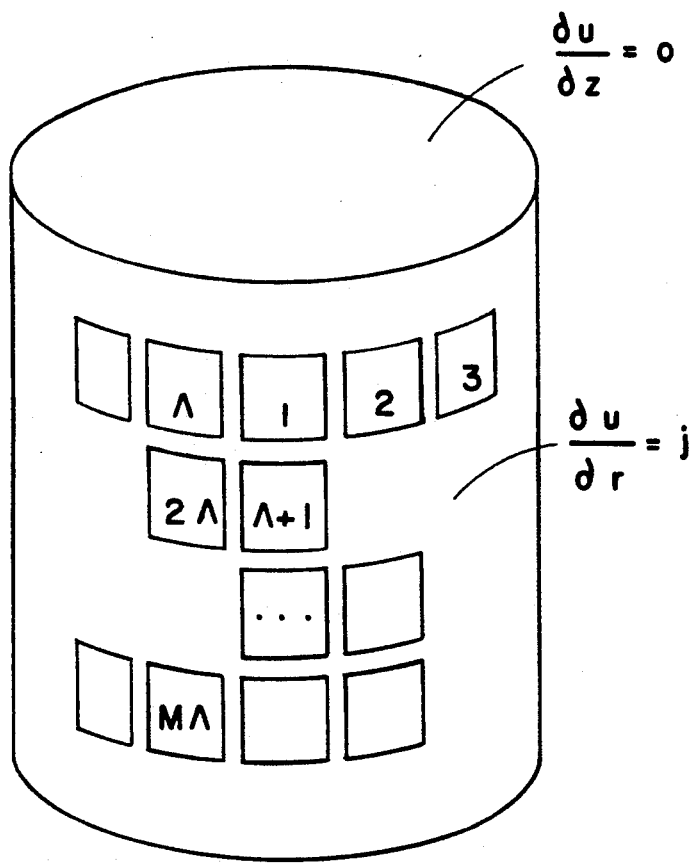
FIG. 1 is a schematic perspective view of a cylindrical body whose internal resistivity is to be imaged according to the present invention, and on which an electrode array is applied.

Consider a right cylindrical volume with a three-dimensional electrode array on the surface as depicted in FIG. 1. Let M denote the number of electrode rings and $\mu$ the ring index. Similarly, let $\Lambda$ denote the number of electrodes on any ring and $\lambda$ the electrode index. Consequently, the total number of electrodes is $L = M\Lambda$.

Using external electronics, patterns of current are established on the electrode array, and as will be seen, measurements resulting from up to $L-1$ orthogonal current patterns over the L electrodes are used to reconstruct the resistivity distribution within the object. Denote the $k^{th}$ current pattern by L-vector $I^k$ and the corresponding voltage measurement by another L-vector $V^k$, so that $$I^k = \begin{bmatrix} I_1^k \\ I_2^k \\ I_3^k \\ \vdots \\ I_L^k \end{bmatrix}; \quad V^k = \begin{bmatrix} V_1^k \\ V_2^k \\ V_3^k \\ \vdots \\ V_L^k \end{bmatrix} \quad (3)$$

We constrain each of the applied current patterns so that $$\sum_{l=1}^{L} I_l = 0,$$

and to preserve this symmetry, we normalize the measured voltages so that $$\sum_{l=1}^{L} V_l^k = 0.$$

We will refer to an operator $R(\rho)$ that maps the applied currents into the measured voltages. We can define another L-vector $U^k$ $$U^k = U(\rho) = \begin{bmatrix} U_1^k \\ U_2^k \\ U_3^k \\ \vdots \\ U_L^k \end{bmatrix} = R(\rho)I^k \quad (4)$$

which represents the predicted voltages on the surface of the tank due to some resistivity guess $\rho$. The forward problem consists of predicting the voltages on L electrodes from knowledge (or an assumption) about the resistivity distribution inside the tank. In the case of a homogeneous cylinder, we can analytically solve for the predicted voltages $U^k$ using increasingly more complete models for the boundary conditions. The more general case would require use of finite difference or finite element techniques to solve the forward problem for an arbitrary resistivity distribution.

The Current Patterns

One of the novel features of this invention is the special patterns of current we apply to the body. One special set of current patterns is composed of the eigenfunctions of the map R for the homogeneous case. In particular, for the right circular cylinder, these patterns are the following tensor products. Here the superscripts denote the index of the current pattern, and the subscripts specify the electrode. The first electrode index, $\mu$, which runs from 1 to M, denotes the row; the second index, $\lambda$, which runs from 1 to $\Lambda$, denotes the angular position. The center of the $(\mu, \lambda)$ electrode is at height $z = \mu$ and angle $\Theta = \Theta_\lambda$.

$$C_{\mu,\lambda}^{m,n} = \cos\frac{m\pi z_\mu}{h} \cos n\theta_\lambda$$

on electrode $(\mu, \lambda)$,
for $m = 0, 1, \ldots, M-1; n = 1, 2, \ldots, \Lambda/2$;

$$S_{\mu,\lambda}^{m,n} = \cos\frac{m\pi z_\mu}{h} \sin n\theta_\lambda$$

on electrode $(\mu, \lambda)$,
for $m = 0, 1, \ldots, M-1; n = 1, 2, \ldots, \Lambda/2$;

$$A_{\mu,\lambda}^{m,n} = \cos m\pi z_\mu/h$$

on electrode $(\mu, \lambda)$,
for $m = 0, 1, \ldots, M-1; n = 0$.
The set
$\{C^{m,n}: m = 0, 1, \ldots, M-1; n = 1, 2, \ldots, \Lambda/2;$
$S^{m,n}: m = 0, 1, \ldots, M-1; n = 1, 2, \ldots, \Lambda/2 - 1;$
$A^{m,n}: m = 0, 1, \ldots, M-1; n = 0\}$ forms a set of $M\Lambda - 1$ mutually orthogonal current patterns. We will refer to these current patterns as the "eigenfunction" current patterns.

A second set of current patterns is composed of those patterns that are best for representing R for the body in question. These patterns are the eigenfunctions of R. A method for obtaining such patterns was disclosed in U.S. Pat. No. 4,920,490 and U.S. patent application Ser. No. 07/734,591. These two references also contain a method for obtaining the patterns that are best for distinguishing the body in question from a given one. These references cover the three-dimensional case as well as the two-dimensional case.

The Fast Reconstruction Process

The second novel feature of this invention is the following fast process by which we reconstruct an approximation to the conductivity.

An outline of a similar process that applies in the two-dimensional case can be found in the paper by M. Cheney, D. Isaacson, J. C. Newell, S. Simske and J. C. Goble, "NOSER: An algorithm for solving the inverse conductivity problem", Internat. J. Imaging Systems and Technology 2, pp. 66–75 (1990). For a three-dimensional problem, this two-dimensional reconstruction process can be used in a naive way to obtain an approximation to the three-dimensional conductivity distribution. In particular, a two-dimensional reconstruction process can be applied to each slice, and the resulting slices displayed as a three-dimensional distribution. This we refer to as a "2.5 - dimensional" reconstruction process. This process, however, ignores the fact that the currents do not confine themselves to a single plane.

In the following, we describe a process that removes this unphysical assumption. This process, which is fully three-dimensional, is partially described in J. C. Goble's Ph.D. thesis, "The inverse problem in three-dimensional electrical impedance tomography", RPI (1990). We give here a complete description of this process.

The current and voltage information can be assembled into the matrix R, which then contains all our data.

Because $R(\rho)$ is self-adjoint, it has at most $$N \leq N_{max} = \frac{L(L-1)}{2} \quad (5)$$

degrees of freedom. We can therefore only hope to recover $N_{max}$ pieces of information about the resistivity distribution. Accordingly, we represent the resistivity in terms of a basis of N known functions with unknown coefficients. We then seek these N unknown coefficients.

Many different bases can be used, but one that is especially simple is the following.

We can subdivide the volume of interest into at most $N_{max}$ voxels, or volume elements, on which the resistivity is considered piece-wise constant. Hence we will compute a resistivity vector of length at most N such that $$\rho(p) = \begin{bmatrix} \rho_1(p) \\ \rho_2(p) \\ \rho_3(p) \\ \cdot \\ \cdot \\ \cdot \\ \rho_L(p) \end{bmatrix} = \sum_{n=1}^{N} \rho_n \chi_n(p) \quad (6)$$

and $$\chi_n(p) = \begin{cases} 1 & \text{if } p \in \text{voxel } n \\ 0 & \text{otherwise.} \end{cases} \quad (7)$$

The design of the three-dimensional mesh on which we represent the conductivity of resistivity deserves careful attention. This is because the ill-conditioning of the reconstruction is affected by the number, size, and position of the voxels (volume elements).

That the size and position are important can be seen by noting that the boundary measurements are most sensitive to the parts of the disk near the boundary. Presumably an optimal mesh would have the size of its voxels at a given location about equal to the size of the smallest object that could be distinguished at that location. The size of the smallest distinguishable object is in turn determined by the measurement precision. For a discussion of the size of the smallest detectable object, see D. G. Gisser, D. Isaacson, and J. C. Newell, "Electric current computed tomography and eigenvalues", SIAM J. Appl. Math 50, pp. 1623-1634 (1990) and D. Isaacson, "Distinguishability of conductivities by electric current computed tomography", IEEE Trans. Med. Imaging MI-5 pp. 91-95 (1986).

The number of voxels is also important. If we try to do the reconstruction on a mesh with more voxels that the number of independent measurements, then the reconstruction problem will be underdetermined. As mentioned above, the number of voxels should be no more than $L(L-1)/2$.

Figure 2:
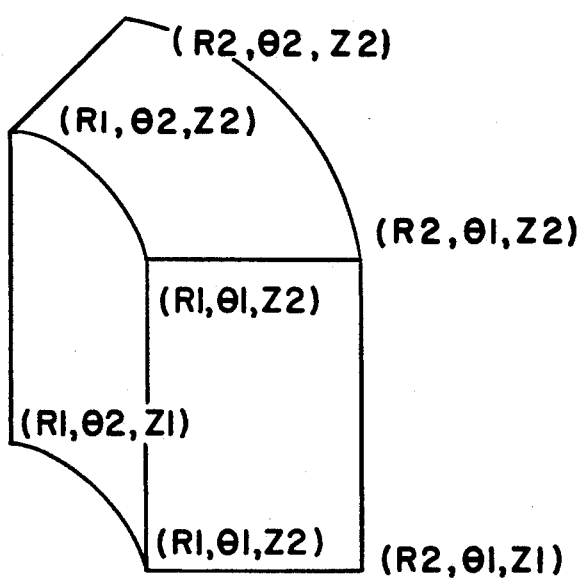
FIG. 2 is a schematic perspective view of a volume element ("voxel") forming part of the body volume.

FIG. 2 depicts the geometry of a typical voxel as used in our existing reconstructor. The inverse problem consists of predicting $\rho(p)$ throughout the body from knowledge of the applied currents and measured voltages.

Two of the present co-inventors, John C. Goble and David Isaacson, in "Optimal current patterns for three dimensional electric impedance tomography" *Proceedings, IEEE Engineering in Medicine and Biology,* 2:463-465, 1989, recently demonstrated images from experimental data using three-dimensional electrode arrays. Efforts of others have focused on correcting existing two-dimensional techniques for out-of-plane current flow, rather than actually obtaining three-dimensional reconstructions (Y. Ziya Ider, Nevzat G. Gencer, Ergin Atalar and Haluk Tosun, "Electrical impedance tomography of translationally uniform cylindrical objects with general cross-sectional boundaries", *IEEE Transactions on Medical Imaging,* 9(1):49-59, 1990; Y. Ziya Ider and Nevzat G. Gencer, "An algorithm for compensating for 3D effects in electrical impedance tomography", *Proceedings, IEEE Engineering in Medicine and Biology,* 2:465-466, 1989).

The goal is to minimize, in the least square sense, an error function $E(\rho)$, $$E(\rho) = \sum_{k=1}^{L-1} ||V^k - U^k||^2 = \sum_{k=1}^{L-1} \sum_{l=1}^{L} (V_l^k - U_l^k)^2. \quad (8)$$

Again $V^k$ represents the voltage experimentally measured for the $k^{th}$ current pattern and $U^k$ represents the predicted voltage for that pattern produced by the forward solver. At a minimum, $$0 = \frac{\partial E}{\partial \rho_n} = F(\rho) = -2 \sum_{k=1}^{L-1} \sum_{l=1}^{L} (V_l^k - U_l^k) \frac{\partial U_l^k}{\partial \rho_n}. \quad (9)$$

We can then compute a new estimate, $$\rho^{i+1}\rho^i - [F'(\rho^i)]^{-1}F(\rho^i), \quad (10)$$

where $$F' = \frac{\partial^2 E}{\partial \rho_i \partial \rho_l} = \begin{bmatrix} \frac{\partial F_1}{\partial \rho_1} & \cdots & \frac{\partial F_1}{\partial \rho_N} \\ \cdot & & \cdot \\ \cdot & & \cdot \\ \cdot & & \cdot \\ \frac{\partial F_N}{\partial \rho_1} & \cdots & \frac{\partial F_N}{\partial \rho_N} \end{bmatrix}. \quad (11)$$

Explicitly, the (n, m)th element of F' is $$F_{n,m}(\rho) = \frac{\partial}{\partial \rho_m} \frac{\partial E(\rho)}{\partial \rho_n} = 2 \sum_{k=1}^{L-1} \sum_{l=1}^{L} \frac{\partial U_l^k(\rho)}{\partial \rho_n} \frac{\partial U_l^k(\rho)}{\partial \rho_m} - 2 \sum_{k=1}^{L-1} \sum_{l=1}^{L} (V_l^k - U_l^k(\rho)) \frac{\partial^2 U_l^k(\rho)}{\partial \rho_n \partial \rho_m}. \quad (12)$$

The overall plan of the 3D reconstruction process is to do one step of Newton's method, using the initial guess $\rho^0$=constant. One step of Newton's method gives us $\rho^1$, which is then displayed using standard display software such as IMAGETOOL software.

For the initial guess, the vector $F(\rho^0)$ and matrix $F'(\rho^0)$ can be obtained analytically. Finding $\rho^1$ from equation (10) therefore involves only inverting the known matrix $F'(\rho^0)$, applying the inverse to the known vector $F(\rho^0)$, and subtracting it from the known vector $\rho^0$.

It turns out that the matrix $F'(\rho^0)$ is ill-conditioned, which means that some of its eigenvalues are large and some are very small. These small eigenvalues prevent us from computing the inverse of $F'$ numerically, because when the eigenvalues are smaller than the machine precision, the computer sets them to zero and concludes that $F'$ is singular. Even if we could invert $F'$, these large eigenvalues would cause small errors in $F(\rho^0)$ to be magnified tremendously.

To get around this problem, we need to regularize $F'$, i.e., modify $F'$ to get rid of its small eigenvalues. There are many ways to do this. The regularization we have used in our tests is based on the meaning of the two terms in the definition (12) of $F'$.

The first term of equation (12), namely, $$A_{n,m} = 2 \sum_{k=1}^{L-1} \sum_{k=1}^{L} \frac{\partial U_l^k}{\partial \rho_n} \frac{\partial U_l^k}{\partial \rho_m}, \tag{13}$$

can be understood as follows. If we apply the $k^{th}$ current pattern and calculate the voltage of the $l^{th}$ electrode, then $\partial U_l^k/\partial \rho_n$ is the change in this voltage when we change the resistivity in the $n^{th}$ voxel. Similarly, $\partial U_l^k/\partial \rho_m$ results from changing the $m^{th}$ voxel. If the $n^{th}$ and $m^{th}$ voxels are near each other, then changes in voltage they produce will be nearly the same, so the product $(\partial U_l^k/\partial \rho_n)(\partial U_l^k/\partial \rho_m)$ will be positive. In particular, this is true if $n=m$. Suppose, on the other hand, that the $n^{th}$ and $m^{th}$ voxels are far from each other. Suppose, further, that the $n^{th}$ voxel is close to the $l^{th}$ electrode, so it has a big effect on the voltage $U_l^k$, which means that $\partial U_l^k/\partial \rho_n$ is relatively large. But then the $m^{th}$ voxel must be far away from electrode 1, so its effect $\partial U_l^k/\partial \rho_m$ is small. Thus the product $(\partial U_l^k/\partial \rho_n)(\partial U_l^k/\partial \rho_m)$ is small [relative to $(\partial U_l^k/\partial \rho_n)(\partial U_l^k/\partial \rho_n)$] if the $n^{th}$ and $m^{th}$ voxel are far from each other. If the mesh is numbered so that nearby voxels have close indices, then the matrix A, whose $(n,m)^{th}$ element is given by (13), has its largest elements on and near the diagonal.

Moreover, these diagonal elements are all positive. The largest diagonal elements are those corresponding to voxels near the boundary, and the smallest correspond to voxels near the center. This variation, between the smallest and largest diagonal elements, is of a reasonable size. In other words, the diagonal of A would itself be a well-conditioned matrix.

The second term of (12), namely $$B_{n,m} = -2 \sum_{k=1}^{L-1} \sum_{l=1}^{L} (V_l^k - U_l^k(\rho)) \frac{\partial^2 U_l^k(\rho)}{\partial \rho_n \partial \rho_m}, \tag{14}$$

is more complicated to interpret and to compute. However, of our guess $\rho^0$ is close to the true $\rho$, then the predicted voltages $U_l^k(\rho^0)$ will be close to the measured voltages $V_l^k$, and $B_{n,m}$ will be small. The regularization we used was to neglect this term entirely, replacing it by a multiple of the diagonal of A. In symbols, $$B_{n,m} \approx \gamma A_{n,m} \delta_{n,m}, \tag{15}$$

where $\delta_{n,m}$ is the Kroenecker delta that is one if $n=m$ and zero otherwise. Here the parameter $\gamma$ is a regularization parameter to be chosen as small as practically possible.

Explicitly, the regularization of $F'$ is $$A_{n,m} \gamma A_{n,m} \delta_{n,m}. \tag{16}$$

By taking $\gamma$ large enough, we can force the regularized $F'$ to be diagonally dominant and positive definite. Since the diagonal matrix $A_{n,m} \delta_{n,m}$ is well-conditioned, by taking $\gamma$ large enough we improve the conditioning of the regularized $F'$. Moreover, this regularization allows us to avoid computing the second derivatives that appear in $F'$.

We select the regularization parameter $\gamma$ empirically to product a suitable balance between stability on the one hand and image contrast and definition of the other. If $\gamma$ is much too small, the reconstruction cannot be carried out at all, for the reasons outlined above. If $\gamma$ is only a little too small, the reconstructed conductivity will overshoot the discontinuity or oscillate. If $\gamma$ is too large, the reconstruction is excessively smooth. In other words, the image is dull and blurred.

Next we turn to the questions of how to compute $\rho^0$, $F(\rho^0)$ and $F'(\rho^0)$.

The following formula can be used for computing $\rho^0$:

$$\rho^0 = \frac{\sum_{k=1}^{L-1} \sum_{l=1}^{L} V_l^k U_l^k(1)}{\sum_{k=1}^{L-1} \sum_{l=1}^{L} [U_l^k(1)]^2}. \tag{17}$$

For computing $F(\rho^0)$ and $F'(\rho^0)$, we need $U_l^k(\rho^0)$ and $\partial U_l^k(\rho^0)/\partial \rho_n$. These quantities, in turn, involve the electric potential in a cylinder due to the applied currents. The general form for the electric potential in a right circular cylinder is $$u(r, \theta, z) = r_0 \rho^0 \sum_{n=1}^{\infty} \left(\frac{r}{r_0}\right)^n \frac{1}{n} (a_{0,n} \cos n\theta + b_{0,n} \sin n\theta) + \tag{18}$$

$$\sum_{m=1}^{\infty} \sum_{n=0}^{\infty} \frac{I_n(m\pi r/h)}{\frac{m\pi}{h} I'_n(m\pi r_0/h)} \cos\left(\frac{m\pi z}{h}\right) (a_{m,n} \cos n\theta + b_{m,n} \sin n\theta),$$

where $I_n$ denotes the modified Bessel function of order n and the coefficients $a_{m,n}$ and $b_{m,n}$ are the appropriate Fourier coefficients. The details can be found in J.C. Goble's dissertation.

We assume that the voltage $U_l^k(\rho^0)$ is the value of the electric potential u at the center of the electrode corresponding to the applied current pattern $I^k$, where the $I^k$ are simply a relabelling of the orthogonal "eigenfunction" current patterns $C^{m,n}$, $S^{m,n}$, $A^{m,n}$ specified above. Therefore, to find $U_l^k(\rho^0)$, we merely evaluate (18) at the surface $r=r_0$ and z and $\Theta$ corresponding to the center of electrode 1.

Finally, to compute the approximation (16) to Jacobian (12), we need $$\frac{\partial U_l^k}{\partial \rho_n}.$$

For this we use the formula $$\frac{\partial U_l^k}{\partial \rho_n} = \sum_{s=1}^{L-1} \frac{\left(F, \frac{\partial U^k}{\partial \rho_n}\right)}{(F, F)} I_l^s, \quad (19)$$

where (A,B) denotes the usual inner product $R^{L-1}$. For computing the inner products in (19) we use the formula $$\left(F, \frac{\partial U^k}{\partial \rho_n}\right) = \frac{1}{(\rho^0)^2} \int_{voxel_n} \nabla_u^s \cdot \nabla_u^k, \quad (20)$$

which is proved in the above-mentioned paper by Cheney, Isaacson, Newell, Simske, and Goble. The integrals in (20) can be done explicitly, using (18) and the fact that in cylindrical coordinates, $$\int \nabla_u \cdot \nabla_v = \int \frac{u_0 v_0}{r^2} + \int u_r v_r + \int u_x v_x. \quad (21)$$

If we have used the special eigenfunction current patterns disclosed above, then the corresponding u is merely a single term of (18). In this case, each integral in (21) factors into a product of one-dimensional integrals over r, Θ, and z. A sample calculation is shown in Goble's dissertation.

We have now shown how to compute all the quantities in our approximation to (10), in which F' is replaced by (16). It remains to invert the matrix (16). This can be done in an efficient way as follows. First we write our approximation to (10) as $$(D^{-\frac{1}{2}} A D^{-\frac{1}{2}} + \gamma I) D^{\frac{1}{2}} [\rho^1 - \rho^0] = -D^{-\frac{1}{2}} F(\rho^0), \quad (22)$$

where D denotes the diagonal of A, A being given by (13). We then find the eigenvalues $\{\lambda_1, \lambda_2, \ldots\}$ and eigenvectors $\{v_1, v_2, \ldots\}$ of the matrix $T = D^{-\frac{1}{2}} A D^{-\frac{1}{2}}$. These eigenvalues and eigenfunctions can be stored and used in the following spectral representation for the inverse of the matrix T:

$$T^{-1} v = \sum_{i=1}^{\infty} \frac{1}{\lambda_i} (v_i, v). \quad (23)$$

The inverse of the matrix $T + \gamma I$ is then obtained by adding $\gamma$ to each eigenvalue in (23), so that $[\rho^1 - \rho^0]$ is given by $$[\rho^1 - \rho^0] = -D^{-\frac{1}{2}} \sum_{i=1}^{\infty} \frac{1}{\lambda_i + \gamma} (v_i, D^{-\frac{1}{2}} F(\rho^0)), \quad (24)$$

where the brackets now denote the usual inner product on $R^N$. We see that this computation merely requires a series of inner products, which can be done very quickly on a parallel machine. Finally, the result of (24) is added to $\rho^0$ to obtain $\rho^1$. The resistivity distribution $\rho^1$ is then displayed.

The present inventors have constructed a three-dimensional saline tank as in FIG. 1 with $\Lambda = 16$ and $M = 4$. The tank radius and height are 15.0 cm and 25.0 cm respectively. The electrodes were constructed of polished 304 stainless steel with an area of 25.8 cm². Conductivity of the saline filing the tank was adjusted to be approximately 750 Ω-cm. Various resistive and conductive targets were introduced into the tank of evaluate the performance of reconstruction algorithms.

A 3.5 cm tall cylindrical resistive target of total volume 45 cm³ was introduced into the test tank at the level of the third row of electrodes. The target was radially located halfway between the electrodes and the center of the tank. The saline in the tank was adjusted to have a resistivity of approximately 150 Ω-cm and the target resistivity was effectively infinite. The instrument disclosed in U.S. Pat. No. 4,920,490, was used to apply current and measure the resulting voltages.

A set of orthogonal current patterns were established on the electrode array, and resulting voltages were recorded.

The images that resulted from the processes described herein appear in the paper of Goble and Isaacson, mentioned above and in J. C. Goble's dissertation.

While a specific embodiment of the invention has been shown and described in detail to illustrate the application of the principles of the invention, it will be understood that the invention may be embodied otherwise without departing from such principles.

What is claimed is:

1. A method for three-dimensionally imaging the interior of a body having an internal resistivity using electrical impedance tomography, comprising:

applying an electrode array having a first selected number of electrodes (L) to the surface of the body;

applying a second selected number of current patterns to the electrode array;

measuring a number of voltage patterns, which is equal to the second selected number, resulting from application of the current patterns;

reconstructing an approximation of the internal resistivity, in which the resistivity $\rho^1$ is expressed in terms of a finite-dimensional basis, and its coefficients in this basis are given by equation (10), $F(\rho^0)$ is a known vector given by equation (9), and a matrix F' is a previously obtained approximation;

$$0 = \frac{\partial E}{\partial \rho_n} = F(\rho) = -2 \sum_{k=1}^{L-1} \sum_{l=1}^{L} (V_l^k - U_l^k) \frac{\partial U_l^k}{\partial \rho_n} \quad (9)$$

$$\rho^{i+1} = \rho^i - [F(\rho^i)]^{-1} F(\rho^i), \quad (10)$$

where $V_l^k$ is the measured voltage pattern and $U_l^k$ is a predicted voltage pattern, E is an error and $\partial U_l^k / \partial \rho_n$ is a change in voltage; and making a three-dimensional image of the interior of the body based on the approximation of the internal resistivity.

2. A method according to claim 1, wherein the matrix F' is defined by $$F_{n,m}(\rho) = \frac{\partial}{\partial \rho_m} \frac{\partial E(\rho)}{\partial \rho_n} = 2 \sum_{k=1}^{L-1} \sum_{l=1}^{L} \frac{\partial U_l^k(\rho)}{\partial \rho_n} \frac{\partial U_l^k(\rho)}{\partial \rho_m} - \quad (12)$$

$$2 \sum_{k=1}^{L-1} \sum_{l=1}^{L} (V_l^k - U_l^k(\rho)) \frac{\partial^2 U_l^k(\rho)}{\partial \rho_n \partial \rho_m}.$$

3. A method according to claim 1, wherein the matrix F' is defined by $$A_{n,m} + \gamma A_{n,m} \delta_{n,m}, \quad (16)$$

where $$A_{n,m} = 2 \sum_{k=1}^{L-1} \sum_{l=1}^{L} \frac{\partial U_l^k}{\partial \rho_n} \frac{\partial U_l^k}{\partial \rho_m}, \quad (13).$$

4. A method according to claim 1, wherein said current patterns are selected from the group consisting of (a) tensor products of discrete trigonometric functions, (b) the best patterns with which to represent the boundary map (R), and (c) the best patterns with which to distinguish the internal resistivity from an estimate for the internal resistivity.

5. A method according to claim 1, where $\rho^0$ is defined by (17);

$$\rho^0 = \frac{\sum_{k=1}^{L-1} \sum_{l=1}^{L} V_l^k U_l^k(1)}{\sum_{k=1}^{L-1} \sum_{l=1}^{L} [U_l^k(1)]^2}. \quad (17)$$

6. A method according to claim 1, including finding and storing a plurality of eigenvectors and a plurality of eigenvalues for the matrix F', inverting the matrix F' for forming a matrix inverse wherein the matrix inverse is computed according to a spectral theorem, and so that the matrix inverse is reduced to a computation of a plurality of inner products.

7. A method according to claim 6, wherein the matrix F' is defined by $$F_{n,m}(\rho) = \frac{\partial}{\partial \rho_m} \frac{\partial E(\rho)}{\partial \rho_n} = 2 \sum_{k=1}^{L-1} \sum_{l=1}^{L} \frac{\partial U_l^k(\rho)}{\partial \rho_n} \frac{\partial U_l^k(\rho)}{\partial \rho_m} - 2 \sum_{k=1}^{L-1} \sum_{l=1}^{L} (V_l^k - U_l^k(\rho)) \frac{\partial^2 U_l^k(\rho)}{\partial \rho_n \partial \rho_m}. \quad (12)$$

8. A method according to claim 6, wherein the matrix F' is defined by $$A_{n,m} + \gamma A_{n,m} \delta_{n,m}, \quad (16)$$

where $$A_{n,m} = 2 \sum_{k=1}^{L-1} \sum_{l=1}^{L} \frac{\partial U_l^k}{\partial \rho_n} \frac{\partial U_l^k}{\partial \rho_m}, \quad (13).$$

* * * * *